United States Patent [19]

Berry et al.

[11] Patent Number: 4,883,453

[45] Date of Patent: Nov. 28, 1989

[54] METHOD OF MANUFACTURING SYNTHETIC VASCULAR GRAFTS

[75] Inventors: John P. Berry, Wirral; David Annis, Bromborough, both of England

[73] Assignees: Ethicoh Inc., Somerville, N.J.; The University of Liverpool

[21] Appl. No.: 90,312

[22] Filed: Aug. 28, 1987

[30] Foreign Application Priority Data

Oct. 27, 1986 [GB] United Kingdom ............... 8625679

[51] Int. Cl.⁴ .......................... A61F 2/04; A61F 2/06; B32B 31/00; F16L 31/00
[52] U.S. Cl. ...................................... 600/36; 623/66; 285/189; 285/260; 156/294; 156/303.1; 156/423
[58] Field of Search .................. 156/294, 303.1, 423; 604/93, 175, 283, 284; 128/912, 334 R, 334 C; 600/36; 285/188, 189, 260; 623/1, 66, 12

[56] References Cited

U.S. PATENT DOCUMENTS

| | | | |
|---|---|---|---|
| 1,823,028 | 9/1931 | Caldwell | 285/189 |
| 2,636,520 | 4/1953 | Geist et al. | 285/260 X |
| 2,638,429 | 5/1953 | Patterson | 156/294 X |
| 3,184,362 | 5/1965 | Litsky et al. | 156/294 X |
| 3,238,605 | 3/1966 | Hills | 285/189 X |
| 4,044,404 | 8/1977 | Martin et al. | 623/66 X |
| 4,601,724 | 7/1986 | Hooven et al. | 623/66 |
| 4,613,168 | 9/1986 | Smith et al. | 285/189 X |
| 4,650,220 | 3/1987 | Grabowski | 285/188 X |

Primary Examiner—Alan W. Cannon
Attorney, Agent, or Firm—Robert L. Minier

[57] ABSTRACT

An aorto-coronary bypass graft comprising a plate portion and at least one tube portion extending from the plate portion, the opening in the tube portion communicating with a corresponding opening in the plate portion.

4 Claims, 3 Drawing Sheets

METHOD OF MANUFACTURING SYNTHETIC VASCULAR GRAFTS

The invention relates to synthetic vascular grafts, and in particular to synthetic vascular grafts for use in aorto-coronary bypass.

In the past, aorto-coronary bypass has been achieved by suturing one end of a vascular graft directly to a hole formed in the aorta and the other end directly to a coronary artery. In multiple bypass operations, the requisite number of vascular grafts are sutured individually to the aorta and respective coronary arteries. One disadvantage of conventional aorto-coronary bypass surgery is that sutures are present at the joint of the aorta and the graft which can lead to thrombosis and occlusion at the site. The suture anastomosis causes hyperplasma; ie., the build up of cells about the sutured area. This build up of cells reduces the diameter of the lumen and in turn reduces the potency of the graft. In some instances the sutured anastomotic area can cause clots to form and also reduce the potency of the graft. Where a multiple bypass operation takes place, there is a further disadvantage that the operation can become undesirably lengthy because of the need for individual attachment of the grafts.

It is an object of the present invention to reduce hyperplasma in the area where the tubular graft meets the aorta.

It is also an object of the present invention to improve the patency of vascular grafts.

It is a further object of the present invention to reduce the time required to conduct multiple bypass operations.

These and other objects of the present invention will become more apparent from the following detailed description and drawings of the graft of the present invention.

According to the invention, there is provided an aorto-coronary bypass graft comprising a flexible plate portion and one or more tube portions extending from the plate portion, the free end of the tube portion communicating through the plate portion with the side of the plate portion remote from the tube portion, the plate portion being adapted to be secured, in use, around its periphery to the wall of an aorta and the free end of the tube being for connection to a respective coronary artery in order to achieve a bypass between the aorta and said coronary artery or arteries.

In the preferred embodiments of the graft of the present invention, there are multiple tube portions. Each tube portion has a first end connected to the plate portion with that connected end being secured to the surface of the plate portion which surface will comprise a portion of the outer surface of the aorta. The opening in the tube portion communicates with the inside of the aorta to which the graft is to be attached through an appropriate opening in the plate portion. This construction provides for a smoother and more uniform surface around the opening to the bypass tube portion and reduces the proliferation of muscle cells around the lumen or opening of the connection between the aorta and the tube portion.

The plate portion may be part cylindrical to be compatible with a portion of an aorta in which the plate portion is to be secured.

The radius of curvature of said plate portion is preferably in the range 1cm to 1.5cm.

The periphery of the plate portion may be elliptical, and the major axis may be in the range 2cm to 4cm, preferably 3cm, in length and the minor axis may be in the range 1cm to 2cm, preferably 1.5cm, in length.

The plate portion is preferably between 1 mm and 2 mm in thickness, and preferably of uniform thickness.

Tube portions are preferably of a diameter in the range 3 mm to 4 mm, and preferably of a wall thickness in the range 300 $\mu$m to 600 $\mu$m.

The tube portions may be extended at an acute angle to the plate portion. The angle may be 45°, although other angles may be preferable depending on requirements.

The tube portions may be of generally uniform thickness but having a portion of greater thickness in the region of the end adjacent the plate portion.

The graft may be of an electrostatically spun fibrous structure. The plate portion may be spun separately from the tube portion, and the portions may be secured together after spinning.

According to a further aspect of the invention there is provided a method of performing an aorto-coronary bypass operation comprising the steps of forming a hole of a predetermined size in an aorta, suturing a plate portion of graft according to the invention to the periphery of the hole, and suturing the free end of the tube portions of the graft to the respective coronary artery or arteries.

According to a still further aspect of the invention, there is provided a method of manufacturing an aorto-coronary bypass graft according to the invention comprising the steps of manufacturing said plate portion, manufacturing the tube portions, forming one or more holes in the plate portion at the hole or holes respectively.

The plate portions may be produced by cutting the plate portion from a tube of diameter similar to that of an aorta. The tube may be a tubular fibrous structure produced by electrostatic spinning.

The tubular portion or portions of the graft may be produced by electrostatic spinning.

The graft is preferably a polymeric fibrous structure.

The step of securing the tube portions to a respective hole in the plate portion may comprise the steps of mounting the tube portion on a rigid tube or rod of external diameter adapted to pass snugly through the hole in the plate portion, applying adhesive to the end of the tube portion to be attached to the plate portion, passing the rigid rod or tube through the hole in the plate portion until the adhesive contacts the surface of the plate portion surrounding the hole, and removing the rigid rod or tube once the plate portion and tube portion are secured together. The adhesive may be anything capable of securing the materials together, and in the case of the graft being of a polymeric fibrous structure, the adhesive may be a solution of the polymer in a solvent.

The application of adhesive to the end of the tube portion is preferably carried out by applying a film of adhesive to a planar surface of a rigid element having a hole formed therethrough of internal dimensions the same as the hole in the plate portion, passing the rigid rod or tube through the hole in the rigid element until the tube portion contacts and collects adhesive, and removing the rigid rod or tube together with the tube portion mounted thereon.

During the step of passing the rigid rod or tube through the plate portion, the plate portion is preferably supported on a base having a hole formed therein of internal dimensions the same as the hole or holes in the plate portion.

The base and the rigid element may be the same.

By way of example, one embodiment of a graft, a method of using a graft and a method of making a graft according to the invention will now be described with reference to the accompanying drawings, in which.

Figure 5A:
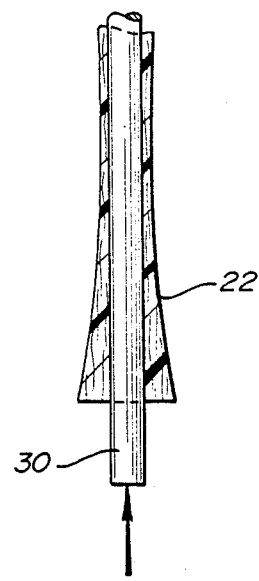
FIG. 5 is a series of drawings illustrating a method of securing a tube portion to a plate portion of a graft according to the invention.
Figure 5B:
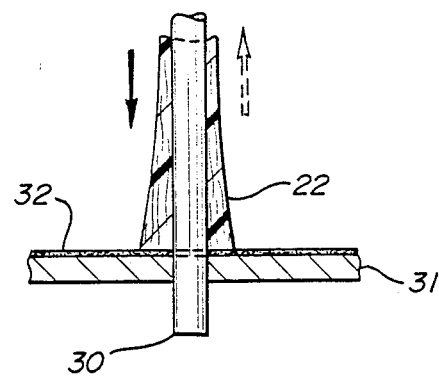
Figure 5C:
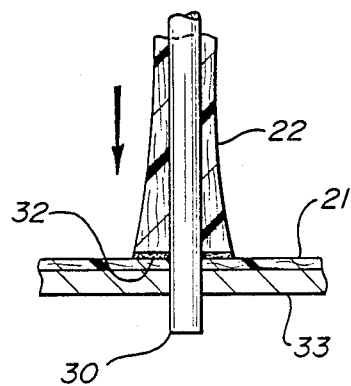

FIG. 5a showing a tube portion mounted on a rod;

FIG. 5b showing adhesive being applied to the tube portion;

FIG. 5c showing the tube portion being secured to the plate portion and

Figure 5D:
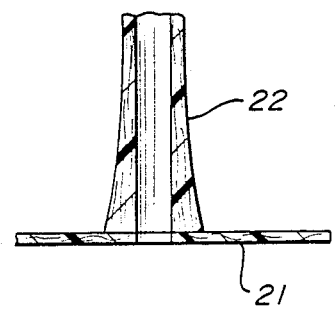

FIG. 5d showing part of the completed graft.

Figure 1:
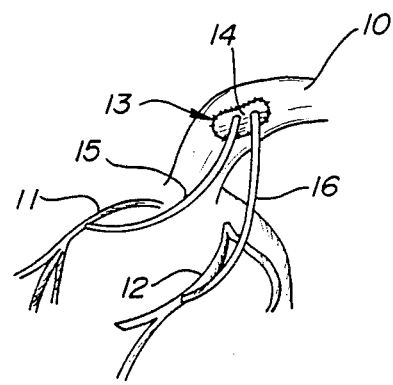
FIG. 1 is a perspective view illustrating a graft according to the invention used to perform two aorto-coronary bypasses.

FIG. 1 illustrates diagrammatically a double bypass between an aorta 10 and two coronary arteries 11 and 12 using a graft 13 according to the invention.

As has been described previously, the conventional method for achieving coronary bypass is to suture a tubular graft directly to the aorta 10 and to a desired coronary artery 11 or 12, and in a case where two bypasses are to be effected, two separate suturing operations are required.

As can be seen in FIG. 1, the graft 13 includes a plate portion 14 and two tube portions 15 and 16. In a double bypass operation using the graft 13, an elliptical hole would be cut in the aorta 10 and the plate portion 14 sutured into the hole. The tube portions 15 and 16 would then be sutured to communicate with the coronary arteries 11 and 12 to produce the required two bypasses. It will be appreciated that suturing of the plate portion 14 would be spaced apart from the openings of the tube portions 15 and 16 and also that in a single suturing operation, both tube portions 15 and 16 can be attached to the aorta 10.

Construction of the graft 13 will be described in more detail with reference to FIG. 2 to 5.

Figure 2:
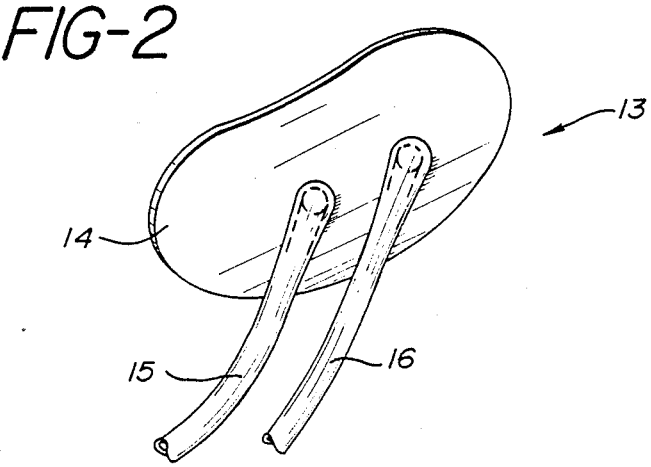
FIG. 2 is an enlarged view of the graft of FIG. 1.

FIG. 2 shows in more detail and on an enlarged scale the graft 13 shown in FIG. 1. The plate portion 14 is, in the preferred embodiment, manufactured separately from the tube portions 15 and 16, the portions being subsequently secured together. The plate portion 14 is elliptical in shape and generally of a size 2 to 4 cm long and 1 to 2 cm wide, a typical length being 3 cm and a typical width being 1.5 cm. In order to be readily compatible with the shape of the aorta, the plate portion 14 is part cylindrical, being cut from a tube of material of substantially the same diameter as the aorta. The radius of curvature is conveniently 1 cm to 1.5 cm.

A preferred material for the plate portion 14 is an electrostatically spun fibrous structure of the type produced by an electrostatic spinning process where polymeric fibres are electrostatically spun around a charged mandrel as has been described in several published specifications such as U.S. Pat. Specification No. 4,044,404, and copending U.K. Application Nos. 2120946A and 2121286A, and copending U.K. Applications 8524541 and 8621150. The plate portion 14 is of a microfibrous structure in the preferred embodiment, with generally randomly oriented fibres of a diameter in the region of 1um. The thickness of the plate portion 14 is that a typical aorta, namely, in the region of 1 to 2 mm thick.

The tube portions 15 and 16 are also formed by electrostatic spinning of polymeric fibres although he fibrous structure in the preferred form differs from the fibrous structure of the plate portion 14. The structure of the tube portions includes circumferentially oriented fibres of a diameter larger than 1um together with circumferentially oriented voids and preferably a substantially impervious layer. Structures of this sort are described in copending British Patent Application No. 8621150. Typical diameters for the tube portions 15 and 16 are 3 to 4 mm internal diameter with a wall thickness in the region of 300 to 600$\mu$m.

Further constructional details and the method of manufacture will now be described with reference to FIGS. 3 to 5.

Figure 3:
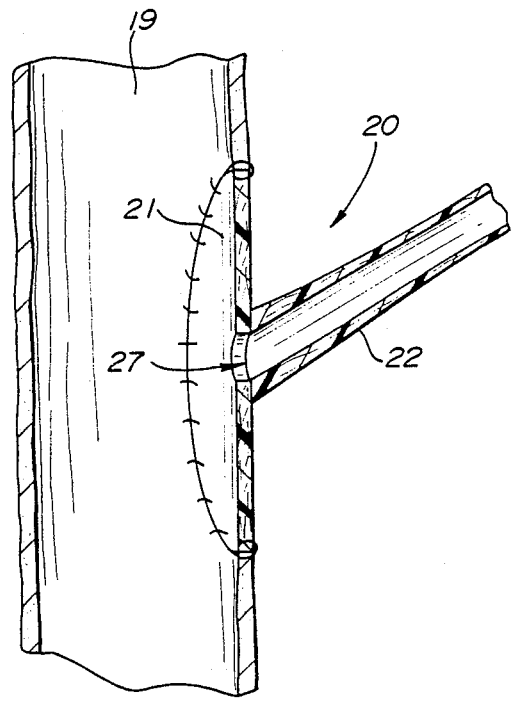
FIG. 3 is a sectional view of an aorta including a graft according to the invention including a single tube portion.
Figure 4:
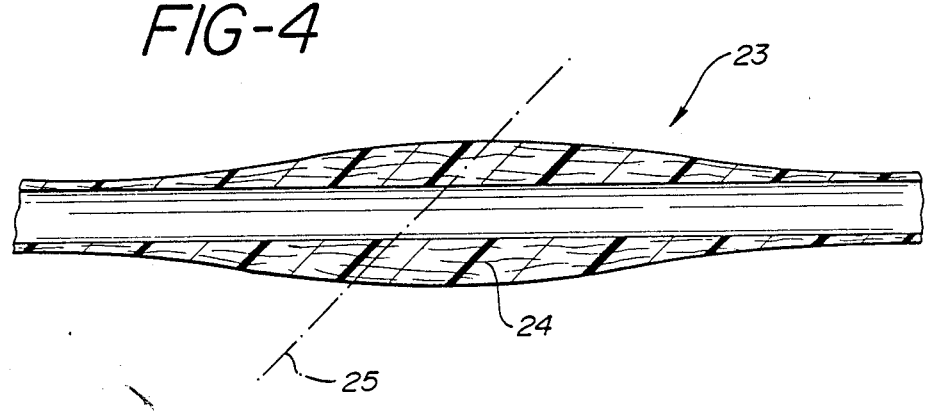
FIG. 4 is a sectional side view showing a tubular fibrous structure from which a tube portion of a graft is taken.

FIG. 3 is a sectional view showing a graft 20 sutured into an aorta 19. The graft 20 has a plate portion 21 and a single tube portion 22 extending from the plate portion 21. The material of the plate portion 21 is the same as the material of the plate portion 14 of the embodiment of FIGS. 1 and 2 previously described and the internal structure of the tube portion 22 is the same as that of the tube portions 15 and 16 of the embodiment of FIGS. 1 and 2 previously described. As can be seen in FIG. 3, the wall of the tube portion 22 is tapered to provide a thicker portion in the region of the plate portion 21. This increases the area of contact between the tube portion 22 and the plate portion 21 to improve securement. It will also be noted that the tube portion 22 leaves the plate portion 21 at an acute angle as may be desirable to avoid undue stress on the graft if the tube portion 22 is to lead to a coronary artery which does not lie on a normal from the aorta. Tapering of the wall thickness of the tube portion 22 is achieved by producing a tubular fibrous structure 23 by electrostatic spinning as shown in FIG. 4 which includes a portion 24 of increased wall thickness. This is readily achieved by electrostatic spinning by directing more material to the area where increased thickness is required. Once the structure of FIG. 4 has been produced, cutting of the tubular structure along the chain dot line 25 will produce the tube portion 22.

As can be seen in FIG. 3, the plate portion 21 is sutured directly to a hole cut in the wall of the aorta 19 and sutures 26 are spaced apart from orifice 27 at the end of the tube portion 22.

The graft 13 or the graft 20 can be made conveniently by securing an associated tube portion to a plate portion as will now be described with reference to FIG. 5. Reference numerals in FIG. 5 will be the same as those used in FIGS. 3 and 4 but for simplicity, the tube portion 22 is shown leaving perpendicularly from the plate portion 21.

The first step, once the tube portion 22 has been spun and cut, is to mount the tube portion 22 on a rigid rod or tube 30. With a a tubular fibrous structure produced by electrostatic spinning, this is readily achieved by swelling the structure with fluid and then shrinking the tube portion 22 on to the tube or rod 30. Once mounted, adhesive in the form of polymeric material in a solution of methyl ethyl ketone or other suitable solvent (a 16% solution is preferred) is applied to the end of the tube portion 22. The solvent is one which is capable of dissolving the material of the tube portion 22 and the plate portion 21 and for this reason, excess solution must be avoided. A convenient way of applying an appropriately thin film of adhesive 32 to a rigid element 31 through which a hole has been formed through which the rod or tube 30 can pass. In this way, as shown in FIG. 5b, a film of adhesive can readily be applied to the end of the tube portion 22.

The next stage is to secure the tube portion 22 to the plate portion 21. In order to do this, the plate portion 21 having had a hole formed in it of internal diameter the same as the internal diameter of the tube portion 22, is laid on a base 33 having a hole formed in it of the same internal dimensions as the hole through the tube portion 22. The rod or tube 30 is then passed through the holes in the plate portion 21 and the base 33 until the tube portion 22 abuts the plate portion 21 and the adhesive bonds together the portions 21 and 22. Once bonded, the rod or tube 30 i withdrawn and the graft lifted off the base 33 a shown in FIG. 5d. The element 31 and the base 33 can conveniently be the same member, perhaps with two holes formed therein one surrounded by an adhesive film and the other without an adhesive film.

Advantages of these embodiments of grafts according to the invention are that only a simple and single union is needed with the aorta by suturing the plate portion to an elliptical hole made in the aorta. Because there are no sutures at the point of attachment of the tube portion or portions at the aortic end, there should be less risk of thrombosis and occlusion at that site. A further advantage is that multiple bypass operations can be carried out from a single plate portion of a graft requiring a single elliptical patch portion to be sutured to the aorta.

It will be appreciated that while the embodiments have been described as formed from electrostatically spun material, it would be possible to produce grafts according to the invention from different materials. It will be appreciated that the foregoing descriptions is by way of example only and that modifications and alterations are possible within the scope of the invention.

We claim:

1. A method of manufacturing an aotro-coronary bypass graft comprising a partially cylindrical plate portion and at least one tube portion extending from said plate portion, said method comprising the steps of forming the plate portion, forming the tube portion, placing at least one hole in the plate portion, mounting the tube portion on a rigid tube or rod of external diameter adapted to pass snugly through the hole in the plate portion, applying adhesive to the end of the tube portion to be attached to the plate portion, passing the rigid rod or tube through the hole in the plate portion until the adhesive contacts the surface of the plate portion surrounding the hole and removing the rigid rod or tube once the plate portion and tube portion are secured together.

2. A method as claimed in claim 1 wherein the application of adhesive to the end of the tubular portion is carried out by applying a film of adhesive to a planar surface of a rigid element having a hole formed therethrough of internal dimensions the same as the hole in the plate portion, passing the rigid rod or tube through the hole in there rigid element until the tube portion contacts and collects adhesive, and removing the rigid rod or tube together with the tube portion mounted thereon.

3. A method as claimed in claim 1 wherein during the step of passing the rigid rod or tube through the plate portion, the plate portion is supported on a base having a hole formed therein of internal dimensions the same as the hole or holes in the plate portion.

4. A method as claimed in claim 3 wherein the base and the rigid element are the same.

* * * * *